US009227991B2

(12) United States Patent
Gou

(10) Patent No.: US 9,227,991 B2
(45) Date of Patent: Jan. 5, 2016

(54) ANTI-TUMOR BIVALENT PLATINUM COMPLEX AND PREPARATION METHOD FOR COMPLEX AND LIGAND OF COMPLEX

(71) Applicant: SOUTHEAST UNIVERSITY, Jiangsu (CN)

(72) Inventor: Shaohua Gou, Jiangsu (CN)

(73) Assignee: SOUTHEAST UNIVERSITY (CN)

( * ) Notice: Subject to any disclaimer, the term of this patent is extended or adjusted under 35 U.S.C. 154(b) by 0 days.

(21) Appl. No.: 14/437,809

(22) PCT Filed: Aug. 29, 2013

(86) PCT No.: PCT/CN2013/082513
§ 371 (c)(1),
(2) Date: Apr. 22, 2015

(87) PCT Pub. No.: WO2014/067336
PCT Pub. Date: May 8, 2014

(65) Prior Publication Data
US 2015/0299237 A1    Oct. 22, 2015

(30) Foreign Application Priority Data
Oct. 29, 2012    (CN) .......................... 2012 1 0422936

(51) Int. Cl.
*C07C 49/92*    (2006.01)
*C07F 15/00*    (2006.01)
*A61K 31/282*    (2006.01)

(52) U.S. Cl.
CPC ........... *C07F 15/0093* (2013.01); *A61K 31/282* (2013.01); *C07F 15/00* (2013.01); *C07F 15/0066* (2013.01)

(58) Field of Classification Search
CPC .................................................. C07F 15/0093
USPC ........................................................ 556/40
See application file for complete search history.

(56) References Cited

FOREIGN PATENT DOCUMENTS

| CN | 101967163 | 2/2011 | ............. C07F 15/00 |
| CN | 102076761 | 6/2011 | ............. C07F 15/00 |
| CN | 102234295 | 11/2011 | ............. C07F 15/00 |
| CN | 102924528 | 2/2013 | ............. C07F 15/00 |
| GB | 2128615 B | * 7/1986 | .......... C07F 15/0093 |
| WO | WO 2004/099224 | 11/2004 | ............. C07F 15/00 |

OTHER PUBLICATIONS

Allan, Robin D., et al. Synthesis and Activity of a Potent N-Methyl-D-aspartic Acid Agonist, *trans*-1-Aminocyclobutane-1,3-dicarboxylic Acid, and Related Phosphonic and Carboxylic Acids, Journal of Medical Chemistry, 1990, 33, 2905-2915 (11 pgs).
Bernhardt, Günther et al., "Carboplatin derivatives with superior antitumor activity compared to the parent compound" *Inorganica Chimica Acta*, 357, 2004, 4452-4466 (15 pgs).
Fujita, Masanobu et al., "Synthesis and $Ca^{2+}$ Antagonistic Activity of 2-[2-[(Aminoalkyl)oxy]-5-methoxyphenyl]-3,4-dihydro-4-methyl-3-oxo-2H-1,4-benzo-thiazines" *Journal of Medical Chemistry*, 1990, 33, 1989-1905 (8 pgs).
Mykhailiuk, Pavel K. et al., "1-Amino-3,3-diflourocyclobutanecarboxylic acid" *Journal of Fluorine Chemistry* 131, 2010, 221-223 (3 pgs).
Liu, Weiping et al., "A Novel Water-Soluble Heptaplatin Analogue with Improved Antitumor Activity and Reduced Toxicity" *Inorganic Chemistry* 2011, 50, 5324-5326 (3 pgs).
Pigou, Paul F., et al., "Convenient Route to 1,3-Disubstituted Cyclobutanes: An Inexpensive Synthesis of 3-Oxocyclobutanecarboxylic Acid" *Journal of Organic Chemistry* 1988, 53, 3841-3843 (3 pgs).
Schaeppi, Ulrich et al., "*cis*-Dichlorociammineplatinum(II) (NSC-119 875): Preclinical Toxicologic Evaluation of Intravenous Injection in Dogs, Monkeys and Mice" *Toxicology and Applied Pharmacology* 25, 230-241 (1973) (12 pgs).
Jianjun, et al., "Synthesis of Carbocyclic-1,1-Dicarboxylic Acids by Phase Transfer Catalysis" *Journal of Beijing Polytechnic University* vol. 24, No. 1, Mar. 1998 (3 pgs).
*Northwest Pharmaceutical Journal*, 2001, 16(2), 67-68 (2 pgs).
*Journal of Zhijiang Academy of Medical Sciences*, 1993 (5) 33-34 (2 pgs).
International Search Report and Written Opinion issued in corresponding PCT Appln. No. PCT/CN2013/082513 dated Dec. 5, 2013, with translation (19 pgs).

* cited by examiner

*Primary Examiner* — Porfirio Nazario Gonzalez
*Assistant Examiner* — Kofi Adzamli
(74) *Attorney, Agent, or Firm* — Hayes Soloway P.C.

(57) ABSTRACT

Platinum complexes containing 3-ketone cyclobutane 1,1-dicarboxylic acid as leaving group for treating cancers and a preparation method of the complexes, one of the platinum complexes is cis-[3-ketone cyclobutane-1,1-dicarboxylic acid radical.diamineplatinum (II)], GSH-5 for short, the chemical structure formula is expressed by formula (1). The other platinum complex is cis-[3-ketone-cyclobutane-1,1-dicarboxylic acid radical.trans-1,2-cyclohexanediamineplatinum (II)], GSH-6 for short, the chemical structure formula is expressed by formula (2). In the formula (2), two chiral carbon atoms marked with * in the trans-1,2-cyclohexanediamine group are both of R forms or S forms.

5 Claims, No Drawings

ANTI-TUMOR BIVALENT PLATINUM COMPLEX AND PREPARATION METHOD FOR COMPLEX AND LIGAND OF COMPLEX

FIELD OF THE INVENTION

The present invention relates to a new-type platinum complex for treating cancer as well as its preparation method, particularly to an antitumor platinum (II) complex containing 3-ketone cyclobutane-1,1-dicarboxylic acid radical as a leaving group.

BACKGROUND OF THE INVENTION

Since clinical application of cis-platinum, researchers have made drug screening on thousands of platinum complexes. Particularly in the recent 20 years, enormous research has been done on antitumor platinum complexes having a new-type structure-activity relationship and their mechanisms, but until now, no platinum drug superior to cis-platinum in overall performance is found. At present, a few antitumor platinum drugs, including cis-platinum, carboplatin and oxaliplatin, have been widely applied in the clinic, but they also show high toxicity and certain drug resistance during clinical use. The shortcomings limit the application of these platinum drugs to a certain extent. Among the existing platinum drugs, cis-platinum no doubt has very strong antitumor activity, but its toxicity is the highest too; although the toxicity of carboplatin is much lower than that of cis-platinum, its inhibiting ability in many tumor cells is disappointing. Given that, changing or adjusting the leaving group or ligand of cis-platinum, carboplatin and oxaliplatin can yet be regarded as an effective way to obtain high-performance and low-toxicity platinum drugs.

SUMMARY OF THE INVENTION

Technical Problem

The object of the present invention is to provide an antitumor platinum (II) complex and the preparation method of the complex and its ligand. The complex provided by the present invention is less toxic than cis-platinum and oxaliplatin. Particularly, complex GSH-5 is less toxic than carboplatin and its antitumor activity is higher than that of carboplatin in general and equivalent to that of cis-platinum and oxaliplatin. It also has desirable water solubility and can overcome drug resistance to some extent. It is a potential effective and low-toxicity antitumor platinum drug.

Technical Solution

In the antitumor bivalent platinum complex provided by the present invention, 3-ketone cyclobutane-1,1-dicarboxylic acid radical is a leaving group ligand of the platinum complex; the platinum complex may be cis-[3-ketone cyclobutane-1,1-dicarboxylic acid radical.diamineplatinum (II)], abbreviation: GSH-5. Its chemical structure is shown in Formula (1):

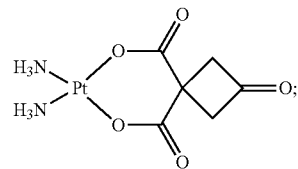

Formula (1)

The platinum complex may also be cis-[3-ketone-1,1-cyclobutane-dicarboxylic acid radical.trans-1,2-cyclohexanediamineplatinum(II)], abbreviation: GSH-6. Its chemical structure is shown in Formula (2):

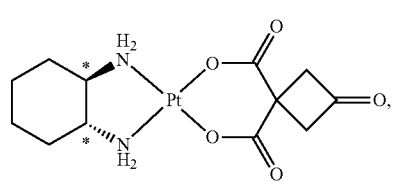

Formula (2)

In Formula (2), the two chiral carbon atoms marked with * in trans-1,2-cyclohexanediamine group are both R configurations or S configurations. The antitumor bivalent platinum complexes shown in Formula (1) and Formula (2) are prepared by the following method:

Firstly, potassium tetrahaloplatinate reacts with ammonia or trans-1,2-cyclohexanediamine in an aqueous solution to obtain cis-[dihalo.bis-ammine (or diamine)platinum (II)] complex; then obtain the target product in an aqueous solution under the condition of being away from light and purging nitrogen by Method A: silver ions are used to remove halide ions from [dihalo.bis-ammine (or diamine)platinum (II)], and the obtained intermediate reacts with 3-ketone cyclobutane-1,1-alkali metal dicarboxylate to obtain the target product; or by Method B: 3-ketone cyclobutane-1,1-silver dicarboxylate reacts with [dihalo.bis-ammine (or diamine)platinum (II)] to obtain the target product.

3-ketone cyclobutane-1,1-alkali metal dicarboxylate involved in Method A is obtained by reacting one equivalent of 3-ketone cyclobutane-1,1-dicarboxylic acid with two equivalents of MOH or $MHCO_3$ in an aqueous solution, or by reacting equal equivalents of 3-ketone cyclobutane-1,1-dicarboxylic acid with $M_2CO_3$ in an aqueous solution, where M is $Na^+$ or $K^+$.

3-ketone cyclobutane-1,1-silver dicarboxylate involved in Method B is prepared by reacting one equivalent of 3-ketone cyclobutane-1,1-dicarboxylic acid with two equivalents of silver nitrate in an aqueous solution.

In the method for preparing the ligand of antitumor bivalent platinum complex, the 3-ketone cyclobutane-1,1-dicarboxylic acid radical is a leaving group ligand of the platinum complex and is prepared by the following reaction route A:

Reaction route A

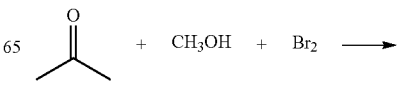

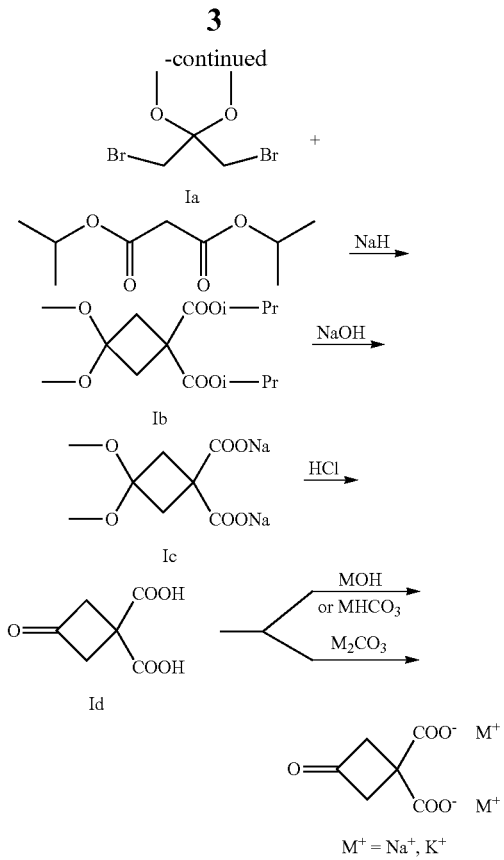

Firstly, acetone, methanol and bromine react to obtain Ia through condensation and bromination, secondly, Ia and diisopropyl malonate take cyclization reaction under the action of sodium hydride to obtain Ib, then Ib is hydrolyzed in a sodium hydroxide solution to obtain Ic, and Ic is acidified by hydrochloric acid to obtain Id, i.e.: 3-ketone cyclobutane-1,1-dicarboxylic acid; the ligand, i.e.: 3-ketone cyclobutane-1,1-dicarboxylic acid radical is obtained by reacting one equivalent of Id and two equivalents of MOH or MHCO$_3$ in an aqueous solution, or by reacting equal equivalents of Id with M$_2$CO$_3$ in an aqueous solution; where M$^+$ is Na$^+$ or K$^+$.

In the foregoing reaction route A, the preparation method of intermediates Ia and Ib has been reported in literatures. Refer to *J. Fluorine Chem.*, 2010, 131, 221 and *J. Org. Chem.*, 1988, 53, 3841.

In literatures, two methods for preparing 3-ketone cyclobutane-1,1-dicarboxylic acid are reported. Refer to *J. Med. Chem.*, 1990, 33, 1905 and Journal of Beijing University of Technology, 1998, 24, 97. Compared with reaction route A, the former reported method has a longer reaction route, involves the steps of oxidation and catalytic hydrogenation in high pressure and has a low yield and high cost; the latter reported method uses ingredients or intermediates, which are restricted chemicals, and has a yield of only 10%, so neither of them are suitable for large-scale industrial production.

The product obtained from reaction route A is confirmed by H NMR (H nuclear magnetic resonance), HR ESI-MS (high resolution electrospray ionization mass spectrometry) and elemental analysis to be 3-ketone cyclobutane-1,1-dicarboxylic acid. Spectral data of the product: $^1$H NMR (D$_2$O) δ: 3.702 ppm (s, 4H); ESI-MS: [M−H]$^-$ 157.0128 (100%). Data of elemental analysis (molecular formula: C$_6$H$_6$O$_5$): theoretical value C, 45.57%; H, 3.82%; measured value C, 45.59%; H, 3.85%.

Beneficial Effects:

The bivalent platinum complexes of the present invention have desirable water solubility, in particular complex GSH-5, and may be made into conventional freeze-dried powder and injection preparation.

Complex GSH-5 and complex GSH-6 provided by the present invention were used to do in vitro antitumor activity research on a series of human tumor cells. The IC$_{50}$ values are shown in Table 1. The data in Table 1 indicates the inhibitory effect of complex GSH-5 on different tumor cells is close to that of cis-platinum to different extent, even better than that of oxaliplatin in some cases, and its anti-cancer effect is much better than that of carboplatin. In addition to showing cytotoxicity on ordinary tumor cells equivalent to that of cis-platinum, complex GSH-5 also has obvious inhibitory effect on human breast cancer drug resistant cell MCF-7 and outperforms cis-platinum in activity.

Mouse-transplanted tumor animal model was adopted to separately observe the inhibitory effect of complex GSH-5 and complex GSH-6 provided by the present invention on animal-transplanted tumor S180 sarcoma and Heps tumor. The relevant data is shown in Table 2 and Table 3 respectively. The result of Table 2 indicates that compared with the model control group, samples GSH-5 and GSH-6 both have significant inhibitory effect (P<0.05) on tumor growth of S180 and body weight of experimental animals; in comparison, the former has better inhibitory effect on tumor growth than the latter does. The result of Table 3 indicates that compared with the model control group, sample GSH-5 has obvious inhibitory effect (P<0.01) on tumor growth of Heps and body weight of experimental animals; in comparison, sample GSH-5 has better inhibitory effect on tumor growth than GSH-6 does.

The toxicity of the two platinum complexes provided by the present invention was preliminarily researched. The result of acute toxicity test done by intravenously injecting sample GSH-5 to mice is 150 mg/kg and the result of sample GSH-6 is 100 mg/kg. The mouse LD$_{50}$ values of cis-platinum, oxaliplatin and carboplatin in literature are 13.40, 14.63 and 139.00 mg/kg respectively (refer to *Toxicology & Applied Pharmacology*, 1973, 25, 230; Northwest Pharmaceutical Journal, 2001, 16(2), 67; Journal of Zhejiang Academy of Medical Sciences, 1993, 15, 33).

The above results indicate the complexes provided by the present invention are less toxic than cis-platinum and oxaliplatin, and particularly, complex GSH-5 is less toxic than carboplatin; the antitumor activity of the complexes provided by the present invention is higher than that of carboplatin in general. Particularly, the antitumor activity of complex GSH-5 is equivalent to that of cis-platinum and oxaliplatin. It also has desirable water solubility and can overcome drug resistance to some extent. It is a potential effective and low-toxicity antitumor platinum drug.

DETAILED DESCRIPTION OF THE EMBODIMENTS

The present invention provides two bivalent platinum complexes with effective antitumor bioactivity and low toxicity. 3-ketone cyclobutane-1,1-dicarboxylic acid radical is a leaving group ligand of the two platinum complexes; one of the complexes is cis-[3-ketone cyclobutane-1,1-dicarboxylic acid radical.diamineplatinum (II)](abbreviation: GSH-5). Its chemical structure is shown in Formula (1):

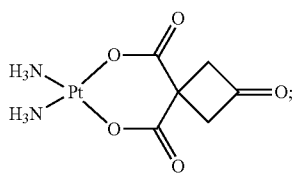

Formula (1)

Another complex is cis-[3-ketone-1,1-cyclobutane-dicarboxylic acid radical.trans-1,2-cyclohexanediamineplatinum (II)](abbreviation: GSH-6). Its chemical structure is shown in Formula (2):

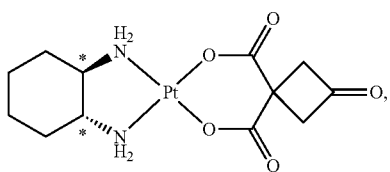

Formula (2)

In Formula (2), the two chiral carbon atoms marked with * in trans-1,2-cyclohexanediamine group are both R configurations or S configurations.

The antitumor bivalent platinum (II) complexes shown in Formula (1) and Formula (2) of the present invention are prepared by the following method: firstly, potassium tetrahaloplatinate reacts with ammonia or trans-1,2-cyclohexanediamine in an aqueous solution to obtain cis-[dihalo.bis-amine (or diamine)platinum (II)] complex; then obtain the target product in an aqueous solution under the condition of being away from light and purging nitrogen by Method A: silver ions are used to remove halide ions from [dihalo.bis-ammine (or diamine)platinum (II)], and the obtained intermediate reacts with 3-ketone cyclobutane-1,1-alkali metal dicarboxylate (sodium salt or potassium salt) to obtain the target product; or by Method B: 3-ketone cyclobutane-1,1-silver dicarboxylate reacts with [dihalo.bis-ammine (or diamine) platinum (II)] to obtain the target product.

3-ketone cyclobutane-1,1-alkali metal dicarboxylate involved in Method A may be obtained by reacting one equivalent of 3-ketone cyclobutane-1,1-dicarboxylic acid with two equivalents of MOH (M is $Na^+$ or $K^+$) or $MHCO_3$ (M is $Na^+$ or $K^+$) in an aqueous solution, or by reacting equal equivalents of 3-ketone cyclobutane-1,1-dicarboxylic acid with $M_2CO_3$ (M is $Na^+$ or $K^+$) in an aqueous solution.

3-ketone cyclobutane-1,1-silver dicarboxylate involved in Method B is obtained by reacting one equivalent of 3-ketone cyclobutane-1,1-dicarboxylic acid with two equivalents of silver nitrate in an aqueous solution.

As for the platinum complex prepared by the method of the present invention, the molecular structures of the compounds are determined by H NMR, HR ESI-MS and elemental analysis and their solubility in water was determined.

Spectral data of complex GSH-5: $^1$H NMR ($d^6$-DMSO): δ 3.717 (s, 4H, $CH_2$ of cyclobutyl), 4.195 (br, 6H, $2\times NH_3$) ppm; ESI-MS: $[M+H]^+$=386.02854 (48%), $[M+Na]^+$=408.01273 (100%). Data of elemental analysis (molecular formula: $C_6H_{10}N_2O_5Pt$): theoretical value C, 18.71%; H, 2.62%; N, 7.27%; Pt, 50.64%; measured value C, 18.66%; H, 2.58%; N, 7.29%; Pt, 50.60%.

Spectral data of complex GSH-6: $^1$H NMR ($d^6$-DMSO): δ1.011-1.044 (m, 2H, $CH_2$ of DACH), 1.195-1.232 (m, 2H, $CH_2$ of DACH), 1.445-1.473 (m, 2H, $CH_2$ of DACH), 1.801-1.841 (m, 2H, $CH_2$ of DACH), 2.056 (m, 2H, $CHNH_2$), 3.718 (s, 4H, $CH_2$ of cyclobutyl), 5.248 (br, 2H, $NH_2$), 5.947-5.977 (br, 2H, $NH_2$) ppm; ESI-MS: $[M+H]^+$=466.09358 (29%), $[M+Na]^+$=488.07568 (100%). DACH stands for the skeleton of trans-1,2-cyclohexanediamine, and cyclobutyl stands for cyclobutyl group. Data of elemental analysis (molecular formula: $C_{12}H_{18}N_2O_5Pt$): theoretical value C, 30.97%; H, 3.90%; N, 6.02%; Pt, 41.92%; measured value C, 31.02%; H, 3.93%; N, 6.03%; Pt, 41.87%.

The solubility of complex GSH-5 in water is 16 mg/mL, and that of complex GSH-6 is 2 mg/mL.

The present invention also provides an efficient method for preparing 3-ketone cyclobutane-1,1-dicarboxylic acid radical as a leaving group ligand. It is prepared by the following reaction route A:

Reaction route A

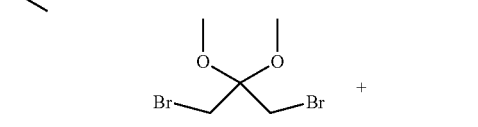

Firstly, acetone, methanol and bromine react to obtain Ia through condensation and bromination, secondly, Ia and diisopropyl malonate take cyclization reaction under the action of sodium hydride to obtain Ib, then Ib is hydrolyzed in a sodium hydroxide solution to obtain Ic, and Ic is acidified by hydrochloric acid to obtain Id (3-ketone cyclobutane-1,1-dicarboxylic acid); the ligand (3-ketone cyclobutane-1,1-dicarboxylic acid radical) may be obtained by reacting one equivalent of Id and two equivalents of MOH (M is $Na^+$ or $K^+$) or $MHCO_3$ (M is $Na^+$ or $K^+$) in an aqueous solution, or by reacting equal equivalents of Id with $M_2CO_3$ (M is $Na^+$ or $K^+$) in an aqueous solution.

The present invention is further described by referring to the following embodiments, but these descriptions are not to limit the present invention. Initiator dihalodiamine (or trans-1,2-cyclohexanediamine) platinum (II) is prepared by a well-known method, which has been described in the description.

(I) Preparation of Compounds

Embodiment 1

Preparation of Complex GSH-5 (Method A)

Suspend cis-diiododiamine platinum (II) (4.83 g, 10 mmol) in 400 mL of water under the condition of being away from light and purging nitrogen, add 30 mL of $AgNO_3$ (3.40 g, mmol) aqueous solution, stir and react at 40° C. in a dark place for 12 hours and filter away silver iodide. Add 40 mL of aqueous solution consisted of 3-ketone cyclobutane-1,1-dicarboxylic acid (1.58 g, 10 mmol) and NaOH (0.80 g, 20 mmol) or $Na_2CO_3$ (1.06 g, 10 mmol) to the above filtrate, stir and react at 40° C. in a dark place for hours, and then filter the solution. Concentrate the filtrate to precipitate out a large amount of solid. Filter, repeatedly wash the solid with water, ethanol and diethyl ether and dry it in vacuum to obtain 2.51 g of white solid, with a yield of 65%.

Embodiment 2

Preparation of Complex GSH-5 (Method B)

Suspend cis-diiododiamine platinum (II) (0.48 g, 1 mmol) in 100 mL of water under the condition of being away from light and purging nitrogen, add 3-ketone cyclobutane-1,1-silver dicarboxylate (0.37 g, 1 mmol), stir and react at 55° C. in a dark place for 12 hours and filter away silver iodide. Concentrate the filtrate to precipitate out a large amount of solid. Filter and dry in vacuum to obtain 0.20 g of white solid, with a yield of 53%.

Embodiment 3

Preparation of Complex GSH-6 (Method A)

Suspend dichloro(trans-1R,2R-cyclohexanediamine) platinum (II) (0.38 g, 1 mmol) in 100 mL of water under the condition of being away from light and purging nitrogen, add 10 mL of $AgNO_3$ (0.34 g, 2 mmol) aqueous solution, stir and react at 40° C. in a dark place for 12 hours and filter away silver chloride. Add the filtrate to 20 mL of aqueous solution consisted of 3-ketone cyclobutane-1,1-dicarboxylic acid (0.16 g, 1 mmol) and KOH (0.11 g, 2 mmol) or $KHCO_3$ (0.20 g, 2 mmol), stir and react at 55° C. in a dark place for 24 hours and then filter the solution. Concentrate the filtrate to precipitate out a large amount of solid. Filter, wash with water and dry in vacuum to obtain 0.24 g of white solid, with a yield of 51%.

Embodiment 4

Preparation of Complex GSH-6 (Method B)

Suspend dichloro(trans-1R,2R-cyclohexanediamine) platinum (II) (0.38 g, 1 mmol) in mL of water under the condition of being away from light and purging nitrogen, add 3-ketone cyclobutane-1,1-silver dicarboxylate (0.37 g, 1 mmol), stir and react at 55° C. in a dark place for 12 hours and filter away silver chloride. Concentrate the filtrate to precipitate out a large amount of solid. Filter and dry in vacuum to obtain 0.31 g of white solid, with a yield of 66%.

Embodiment 5

Preparation of 3-Ketone-1,1-Cyclobutane-Dicarboxylic Acid (Id) (Reaction Route A)

Intermediates Ia and Ib are prepared by the methods described in literatures. Dissolve 15 g of intermediate Ib in 200 mL of ethanol, add 30 mL of NaOH (12 g, 0.3 mol) aqueous solution, reflux the reaction solution for 3 hours, filter it in vacuum to obtain white solid and wash it with ethanol for 3 times to obtain intermediate Ic. Dissolve intermediate Ic in 100 mL of 6M hydrochloric acid solution, and stir and react at room temperature overnight. Extract the reaction solution with 400 mL of ethyl acetate, dry the organic phase with anhydrous sodium sulfate, then concentrate it to about 10 mL, add 300 mL of petroleum ether or diethyl ether and keep the mixed solution in a refrigerator overnight to precipitate out light yellow solid. The crude product is dissolved in water, heated, decolored by activated carbon and recrystallized to obtain white solid product Id, with a yield of 89%.

Embodiment 6

Preparation of Ligand (3-Ketone-1,1-Cyclobutane-Dicarboxylic Acid Radical) (Reaction Route A)

The ligand may be obtained by the following three methods:
(i) Obtained by dissolving Id (1.58 g, 10 mmol) and NaOH (0.80 g, 20 mmol) or KOH (1.12 g, 20 mmol) in 40 mL of aqueous solution;
(ii) Obtained by dissolving Id (1.58 g, 10 mmol) and $NaHCO_3$ (1.68 g, 20 mmol) or $KHCO_3$ (2.00 g, 20 mmol) in 50 mL of aqueous solution; or
(iii) Obtained by dissolving Id (1.58 g, 10 mmol) and $Na_2CO_3$ (1.06 g, 10 mmol) or $K_2CO_3$ (1.38 g, 10 mmol) in 50 mL of aqueous solution.

Embodiment 7

Preparation of 3-Ketone Cyclobutane-1,1-Silver Dicarboxylate

Suspend 3-ketone cyclobutane-1,1-dicarboxylic acid (1.58 g, 10 mmol) in 100 mL of water in a dark place, add 20 mL of $AgNO_3$ (3.40 g, 20 mmol) aqueous solution, stir and react at room temperature in a dark place for 1-2 hours, filter, wash with water to precipitate out white solid and dry it in vacuum to obtain 3.41 g of the solid, with a yield of 92%.

(II) In Vitro Cytotoxicity Test of the Complexes

Test Example 1

This test example adopts MTT method to conduct cytotoxicity test on the complexes of the present invention and the common clinical anti-cancer platinum drugs.

MTT Method:

Select cells in logarithmic phase, count them and inoculate them in a 96-well culture plate, at about 8000-10000 cells/well. Cultivate the cells overnight, administrate drug after the cells are attached to the wall, and set a drug group, a positive control group and a negative control group. The complex to be tested is prepared into a stock solution by using 5% glucose aqueous solution. Before use, it is diluted with cell culture medium into solutions at a series of concentrations. Each concentration has 3 duplicate wells. Cultivate for 48 hours after administration of drug, add 20 µL of 5 mg/mL MTT, incubate at 37° C. for 4 hours, remove the supernate and add 150 µL of DMSO-dissolved formazan. Determine OD value of every well at 490 nm wavelength by microplate reader, calculate inhibition rate, draw a concentration-inhibition rate curve and calculate value $IC_{50}$.

This test example adopts MTT method to test the cytotoxicity of complexes GSH-5 and GSH-6 to multiple kinds of human tumor cells (human lung cancer cell A549, human umbilical vein endothelial cell HUVEC, human breast cancer cell MCF-7, human breast cancer drug resistant cell MCF-7, human breast cancer cell MDA-MB-231, human gastric adenocarcinoma cell BGC823, human hepatoma carcinoma cell HepG-2, human erythroleukemia cell K562, human acute promyelocytic leukemia cell NB4, human large cell lung cancer cell NCI-H460 and human hepatoma carcinoma cell SMMC-7721), using cis-platinum, oxaliplatin and carboplatin as positive controls. As the prepared platinum complexes have desirable water solubility, 5% glucose solutions of the samples are used for testing. The results are shown in Table 1.

TABLE 1

$IC_{50}$ values of the complexes on some human tumor cells (µM)

| Tumor cell | $IC_{50}$ (µM) | | | | |
|---|---|---|---|---|---|
| | GSH-5 | GSH-6 | Cis-platinum | Oxaliplatin | Carboplatin |
| A549 | 36.33 | 47.53 | 16.61 | 70.31 | 137.42 |
| HUVEC | 30.18 | 68.94 | 11.24 | 16.29 | 101.58 |
| MCF-7 | 33.43 | 34.23 | 32.92 | 25.71 | 109.47 |

TABLE 1-continued $IC_{50}$ values of the complexes on some human tumor cells (µM)

| Tumor cell | $IC_{50}$ (µM) | | | | |
|---|---|---|---|---|---|
| | GSH-5 | GSH-6 | Cis-platinum | Oxaliplatin | Carboplatin |
| MCF-7 drug resistant | 20.78 | 1348.48 | 32.94 | 351.35 | 457.41 |
| MDA-MB-231 | 31.05 | 36.33 | 18.27 | 29.12 | 93.29 |
| BGC823 | 8.82 | 8.90 | 5.44 | 7.92 | 43.21 |
| HepG2 | 9.67 | 31.63 | 2.11 | 27.22 | 99.10 |
| K562 | 15.43 | 35.97 | 10.93 | 23.628 | 117.71 |
| NB4 | 2.18 | 3.10 | 1.27 | 52.82 | 12.59 |
| NCI-H460 | 7.45 | 11.91 | nd* | 23.08 | 30.58 |
| SMMC-7721 | 10.39 | 216.50 | nd* | 32.32 | 52.66 |

*Not determined.

(III) In Vivo Tumor Inhibitory Effects of the Complexes

Test Example 2

This test example adopts mouse-transplanted tumor animal model method to test the inhibitory effects of the complexes provided by the present invention on animal-transplanted tumor S180 sarcoma and Heps tumor.

Get ICR mice and inoculate solid tumor according to the research method of transplanted tumor. Weigh the mice 24 hours after the inoculation and randomly divide them into 7 groups, 8 mice per drug group. Administrate drug by intravenous injection for the first time 24 hours ($d_1$) after the inoculation, administrate drug once every other day for a total of 4 times, at a dose of 0.4 ml/20 g each time. Kill and weigh the tumor-bearing mice days ($d_{10}$) after the inoculation, separate and weigh the tumor mass, and conduct statistical treatment of all the obtained data (t-test). The inhibitory effect of the complexes on mouse-transplanted tumors S180 and Heps is shown in Table 2 and Table 3 respectively.

TABLE 2

Inhibitory effect of the complexes on mouse-transplanted tumor S180 ($\bar{X} \pm SD$)

| Group | Dose (mg/kg) | Body weight (g) | | Number of Animal | | Tumor weight (g) | Tumor inhibition rate (%) |
|---|---|---|---|---|---|---|---|
| | | Before administration | After administration | Beginning of the test | End of the test | | |
| Model control group | — | 23.80 ± 1.33 | 23.80 ± 1.78 | 10 | 10 | 0.97 ± 0.17 | |
| GSH-5 | 30 mg/kg | 22.80 ± 1.94 | 18.13 ± 1.76** | 10 | 8 | 0.07 ± 0.10** | 92.80 |
| | 15 mg/kg | 19.25 ± 0.66 | 22.50 ± 1.91* | 10 | 10 | 0.36 ± 0.15** | 62.76 |
| GSH-6 | 20 mg/kg | 19.50 ± 2.35 | 18.60 ± 2.24** | 10 | 10 | 0.52 ± 0.13** | 46.61 |
| | 10 mg/kg | 22.80 ± 1.33 | 20.60 ± 2.50** | 10 | 10 | 0.65 ± 0.14** | 33.13 |

*P < 0.05 compared with the model control group,
**P < 0.01 compared with the model control group.

TABLE 3

Inhibitory effect of the complexes on mouse-transplanted tumor Heps ($\overline{X} \pm SD$)

| Group | Dose (mg/kg) | Body weight (g) Before administration | Body weight (g) After administration | Number of Animal Beginning of the test | Number of Animal End of the test | Tumor weight (g) | Tumor inhibition rate (%) |
|---|---|---|---|---|---|---|---|
| Model control group | — | 19.75 ± 1.48 | 27.63 ± 2.83 | 8 | 8 | 1.30 ± 0.45 | |
| GSH-5 | 50 mg/kg | 19.50 ± 0.71 | 13.50 ± 0.50** | 8 | 2 | 0.00** | 100 |
| | 25 mg/kg | 19.25 ± 0.66 | 22.13 ± 3.52** | 8 | 8 | 0.39 ± 0.32** | 70.08 |
| GSH-6 | 50 mg/kg | 19.50 ± 2.35 | — | 8 | 0 | — | — |
| | 25 mg/kg | 19.13 ± 1.69 | 18.10 ± 1.10** | 8 | 8 | 0.84 ± 0.17 | 35.44 |

**P < 0.01 compared with the model control group.

(IV) Preliminary Toxicity of the Complexes

Test Example 3

Select 50 Kunming mice of clean grade, 25 males and 25 females, with body weight 18~22 g, randomly divide them into 5 groups, 10 mice in each group, and fast for 12 hours. Dissolve complex GSH-5 and complex GSH-6 in 5% glucose solution and inject (iv) the solution to mice via caudal vein in 5 doses. The acceptance capacity of an animal is 0.4 mL/20 g. Observe continuously for 14 days after administration, and record toxic symptoms and death of mice. Calculate the experiment results according to Bliss method to obtain $LD_{50}$ values of complex GSH-5 and complex GSH-6 to mice (iv), which are mg/kg and 100 mg/kg (95% confidence limit) respectively.

The invention claimed is:

1. An antitumor bivalent platinum complex, wherein, 3-ketone cyclobutane-1,1-dicarboxylic acid radical is a leaving group ligand of the platinum complex; the platinum complex may be cis-[3-ketone cyclobutane-1,1-dicarboxylic acid radical.diamineplatinum (II)], abbreviation: GSH-5, and its chemical structure is shown in Formula (1):

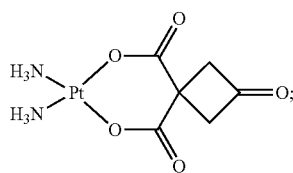

Formula (1)

the platinum complex may also be cis-[3-ketone-1,1-cyclobutane-dicarboxylic acid radical.trans-1,2-cyclohexanediamineplatinum(II)], abbreviation: GSH-6, and its chemical structure is shown in Formula (2):

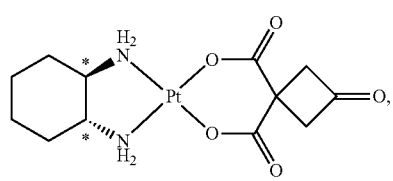

Formula (2)

in Formula (2), two chiral carbon atoms marked with * in trans-1,2-cyclohexanediamine group are both R configurations.

2. A method for preparing the antitumor bivalent platinum complex according to claim 1, wherein, the antitumor bivalent platinum complexes shown in Formula (1) and Formula (2) are prepared by the following method:

firstly, potassium tetrahaloplatinate reacts with ammonia or trans-1,2-cyclohexanediamine in an aqueous solution to obtain cis-[dihalo.bis-ammineplatinum (II)] or cis-[dihalo.diamineplatinum (II)]; then obtain target product in an aqueous solution under the condition of being away from light and purging nitrogen by Method A: silver ions are used to remove halide ions from cis-[dihalo.bis-ammineplatinum (II)] or cis-[dihalo.diamineplatinum (II)], and obtained intermediate reacts with 3-ketone cyclobutane-1,1-alkali metal dicarboxylate to obtain the target product; or by Method B: 3-ketone cyclobutane-1,1-silver dicarboxylate reacts with cis-[dihalo.bis-ammineplatinum(II)] or cis-[dihalo.diamineplatinum (II)] to obtain the target product.

3. The method for preparing the antitumor bivalent platinum complex according to claim 2, wherein, 3-ketone cyclobutane-1,1-alkali metal dicarboxylate involved in Method A is obtained by reacting one equivalent of 3-ketone cyclobutane-1,1-dicarboxylic acid with two equivalents of MOH or $MHCO_3$ in an aqueous solution, or by reacting equal equivalents of 3-ketone cyclobutane-1,1-dicarboxylic acid with $M_2CO_3$ in an aqueous solution, where M is $Na^+$ or $K^+$.

4. The method for preparing the antitumor bivalent platinum complex according to claim 2, wherein, 3-ketone cyclobutane-1,1-silver dicarboxylate involved in Method B is obtained by reacting one equivalent of 3-ketone cyclobutane-1,1-dicarboxylic acid with two equivalents of silver nitrate in an aqueous solution.

5. A method for preparing the antitumor bivalent platinum complex according to claim 2, wherein, 3-ketone cyclobutane-1,1-dicarboxylic acid radical is a leaving group ligand of the platinum complex and is prepared by the following reaction route A:

Reaction route A

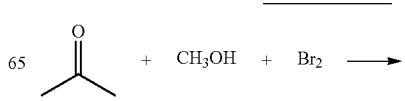

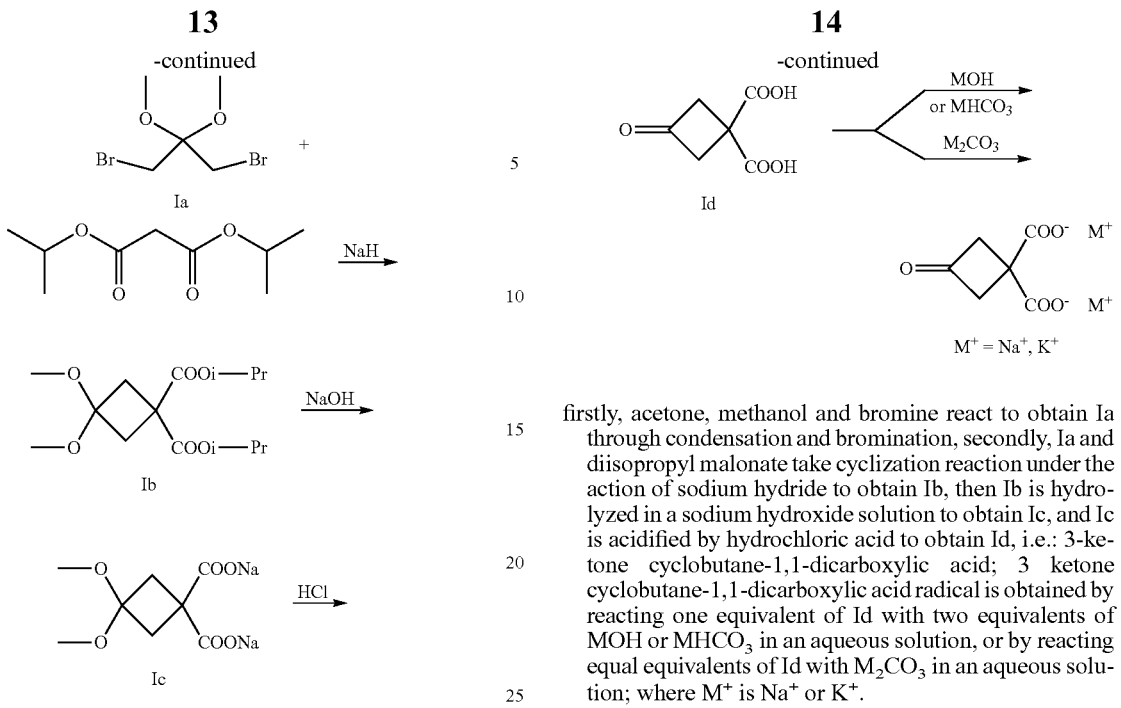

firstly, acetone, methanol and bromine react to obtain Ia through condensation and bromination, secondly, Ia and diisopropyl malonate take cyclization reaction under the action of sodium hydride to obtain Ib, then Ib is hydrolyzed in a sodium hydroxide solution to obtain Ic, and Ic is acidified by hydrochloric acid to obtain Id, i.e.: 3-ketone cyclobutane-1,1-dicarboxylic acid; 3 ketone cyclobutane-1,1-dicarboxylic acid radical is obtained by reacting one equivalent of Id with two equivalents of MOH or $MHCO_3$ in an aqueous solution, or by reacting equal equivalents of Id with $M_2CO_3$ in an aqueous solution; where $M^+$ is $Na^+$ or $K^+$.

* * * * *